United States Patent [19]

Stout

[11] Patent Number: 4,572,834
[45] Date of Patent: Feb. 25, 1986

[54] BIOLOGIC AND METHOD OF PREPARING SAME

[75] Inventor: Robert L. Stout, Overland Park, Kans.

[73] Assignee: Clinical Reference Laboratory, Inc., Lenexa, Kans.

[21] Appl. No.: 598,744

[22] Filed: Apr. 10, 1984

[51] Int. Cl.[4] ..................... A61K 35/14; A61K 39/00
[52] U.S. Cl. ........................................ 424/86; 424/89; 424/101
[58] Field of Search ................ 424/86, 89, 101; 435/241

[56] References Cited

U.S. PATENT DOCUMENTS

| | | | |
|---|---|---|---|
| 2,136,131 | 12/1938 | Green | 424/89 |
| 2,271,818 | 2/1942 | Green | 424/89 |
| 2,271,819 | 2/1942 | Green | 424/89 |
| 3,128,230 | 4/1964 | Heinbach | 424/86 |
| 3,293,130 | 12/1966 | Slater et al. | 424/89 |
| 3,376,198 | 4/1968 | Petersen et al. | 424/86 |
| 3,465,077 | 9/1969 | Baker | 424/89 |
| 3,577,525 | 5/1971 | Baker | 424/89 |
| 3,892,627 | 7/1975 | Simons et al. | 424/89 |
| 3,911,108 | 10/1975 | Singh | 424/86 |
| 4,193,990 | 3/1980 | Appel et al. | 424/89 |
| 4,193,991 | 3/1980 | Appel et al. | 424/89 |
| 4,303,645 | 12/1981 | Carmichael et al. | 424/89 |

*Primary Examiner*—Shep K. Rose
*Attorney, Agent, or Firm*—Schmidt, Johnson, Hovey & Williams

[57] ABSTRACT

A method is described for the production of large quantities of biologic which serves as an immunomodulator and also to decrease the concentration of serum cholesterol and triglycerides. In practice, an animal such as a goat is injected with a virus (preferably a normally immunosuppressive Parvovirus) and allowed to react to the virus for a period of time to generate the biologic in its blood serum; blood is then withdrawn from the animal and the serum fraction thereof, containing the desired biologic, can be used in fractionated or more highly purified form. Examples are also provided of use of the biologic as an immunostimulant and for reducing serum cholesterol and triglycerides.

4 Claims, 3 Drawing Figures

FIRST STAGE CHROMATOGRAPHY PROFILE

SECOND STAGE CHROMATOGRAPHY PROFILE

THIRD STAGE CHROMATOGRAPHY PROFILE

BIOLOGIC AND METHOD OF PREPARING SAME

BACKGROUND OF THE INVENTION

1. Field of the Invention

The present invention is broadly concerned with a method for producing a higly useful biologic through the viral immunization of an animal such as a goat. More particularly, it is concerned with such a production method, along with a method of treating mammals using the biologic, wherein, in preferred forms, the goat or other test animal is treated with a virus such as a parvovirus which is normally immunosuppressive in a permissive host.

2. Description of the Prior Art

Vaccines have been in use since Edward Jenner (1749–1823) first recognized that people exposed to non-virulent strains of microorganisms could be protected against infection by the related virulent strains. His vaccination of patients with exudate of cowpox sores provided those same patients with partial protection against smallpox. Numerous vaccines have subsequently been prepared and used in both humans and animals. Immunization has been accomplished by vaccination with a suspension of live, attenuated, or killed organisms or specific protein, glycoprotein or surface material from various bacteria, rickettsiae, or viruses. These would include vaccines against anthrax, rabies, typhoid, cholera, smallpox, measles, mumps, pertussis, plague, and polio. The vaccine in each case has been intended to provide protection against a specific pathogen. While vaccination may provide long term specific protection it may or may not produce short term immunosystem modulation. The immune system responds to challenge via vaccination or infection by increased activity. This may result in the short term production of antigen non-specific immunoregulatory modulators such as interferon, interleukins, and other various lymphokines.

The rationale for a system that becomes active only in response to a specific challenge is simple. If the immune system operated at a high pitch of activity all the time, it would age prematurely and no longer provide the systematic protection it was evolved to deliver. Another possible complication with an unusually active immune system could be the initiation of autoimmune reactions in which the system starts acting against itself, resulting in the destruction of normal tissue. Arthritis is exemplary of this particular condition.

Increased activity of the immune system by virtue of improper regulation could furthermore result in an inability to ellicit an appropriate response. As an example, a massive response to a splinter in a finger would be completely inappropriate, just as no response to a major infection would be equally inappropriate.

Immunomodulation may provide a regulatory-directed approach at self-healing, particularly with respect to such intractable diseases as cancer. For this to occur two minimal criteria must be met. The immune system must be sufficiently intact to respond to the regulator(s), and secondly, the system under appropriate stimulation must have T-cells, B-cells and Natural Killer cells present that are capable of responding to the target antigen(s) or cell(s). In such an instance, however, a nonspecific immunomodulator could potentially serve to "turn on" the immune system and initiate healing.

A number of immunomodulators have previously been isolated and described and these appear to belong to one of three general groups, namely the interferons, the interleukins and the corticosteroids and leukotrienes.

The interferons are a family of glycoproteins normally produced in response to a viral infection and are produced by leukocytes and fibroblasts. There are three main types, alpha, beta and gamma. They have molecular weights in the range of 15,000 to 40,000 daltons. Recently they have been produced by recombinant DNA techniques. The interferons have been found to have an absolute specie specificity, and are only effective in the specie that produced it.

The second group of immunomodulators are the interleukins. They are a family of glycoproteins that are produced by white cells. It is believed that the lymphokines cause the activation of Natural Killer cells and B-cells, and act in the initiation and propagation of the specific sequences of cellular interactions that are now recognized as the immune response. These growth promoters and activators participate in the generation of immunoreactive cells. The lymphokines are antigen non-specific in that they activate all T and B cells in anticipation of the presentation of an antigen or a cell. The apparent molecular weights are in the range of 15,000–50,000 daltons.

The third type of regulators are the corticosteroids and the leukotrienes, which act as regulators in inflammation. When produced in atypical amount, the leukotrienes can cause immediate type hypersensitivity and anaphylaxis. They are principally oxygenated products of archidonic acid. In contract the corticosteroids decrease immune system activity. Both corticosteroids and leukotrienes are small molecular weight compounds in comparison to the interleukins and interferons.

All of the immulogical regulators produced commercially are extracts or concentrates of tissue culture fluids from mitogen stimulated lymphoid and myleloid cells. The exception to this had been the IL-2 which has been produced by genetic engineering. The other immulogical modulators that have been artificially produced are the interferons. The difficulty with each of these production methods is that the individual reagents being produced do not reproduce the plethoric effect seen in vivo. No practical method has heretofore been discovered to produce a plurality of the immunoregulators together in the same proportions as they would normally be produced in response to infection or cancer in situ. Additionally the cost of prior known production methods has been considerable, thereby further limiting the utility of immunomodulators.

Cardiovascular disease is one of the principal causes of death in the United States, accounting for approximately one million deaths a year. One of the main contributory factors to the development of coronary heart disease is the presence of high levels of serum cholesterol. While serum cholesterol concentrations may be altered by diet, in humans the majority of cholesterol is synthesized in the liver and then distributed by low density lipoproteins. As a consequence, control of serum cholesterol concentrations solely by diet alone is very difficult if not impossible.

Currently there is only one medication, Cholestyramine, that has proven to be effective in lowering high serum cholesterol concentrations. Cholestyramine is an anion exchange resin that binds bile acids, resulting in a decreased reabsorption of the bile acids and the associated dietary cholesterol that they would normally carry back via the liver portal system. While use of Cholestyramine is indicated in certain patients, its use is limited because it may cause further increases in the serum triglyceride levels.

SUMMARY OF THE INVENTION

The present invention is broadly concerned with a unique method for the production of a biologic useful as an immunomodulator; moreover, it has been found that the biologic also serves to significantly decrease serum cholesterol and triglyceride levels in patients.

Broadly stated, the method of the invention comprises the steps of injecting a virus such as a parvovirus into an animal, and permitting the injected animal to react to the presence of the virus for a period of time in order to develop in the animal's blood serum biologic in sufficient quantity and/or activity that 50 microliters of the animal's serum, when added to an in vitro human white blood cell culture containing $2-4 \times 10^5$ white blood cells and followed by 3 days incubation at 37° C. under a 5% $CO_2$/95% air atmosphere, will give rise to at least about a 50% increase in T-helper and Natural Killer cells in the biologic-supplemented cell culture, as compared with an otherwise identical and identically cultured in vitro cell culture having added thereto 50 microliters of serum from a normal animal of the same species as the injected animal. The final step in the method involves recovering serum from the injected animal which contains the desired biologic.

In particularly preferred forms of the invention, the animal in question is a goat, and the virus injected is a Parvovirus of a type which is immunosuppressive in a normal permissive host animal (e.g. a cat or dog) for the Parvovirus. Thus, in the presently preferred method of the invention, use is made of a normally immunosuppressive virus in a non-permissive host for the virus; quite surprisingly however, this serves to develop an immunostimulative biologic in the injected animal's serum which has the salutary effects outlined above.

In other forms of the invention, the injected animal can be selected from the group consisting of goats, horses, sheep, rabbits and monkeys, with the period of time after injection of the virus being at least about one month.

The injected and immunized animal's serum can be used in relatively crude form, such as after only conventional ammonium sulfate fractionation. In other instances, however, the fractionated serum is subjected to further isolation procedures, in order to substantially purify the biologic.

In actual practice, a number of test goats are normally immunized with Parvovirus, and the serum of these goats is tested after an appropriate time (e.g. about 3 months) for the presence of biologic using the standard outlined above. Those animals which are positives, i.e., their serum exhibits the biologic in the manner defined, are then bled and their serum, containing the biologic, is recovered.

The biologic of the invention can be used for a wide variety of mammals such as man and domesticated animals in order to obtain beneficial results.

DESCRIPTION OF THE PREFERRED EMBODIMENTS

Figure 1:
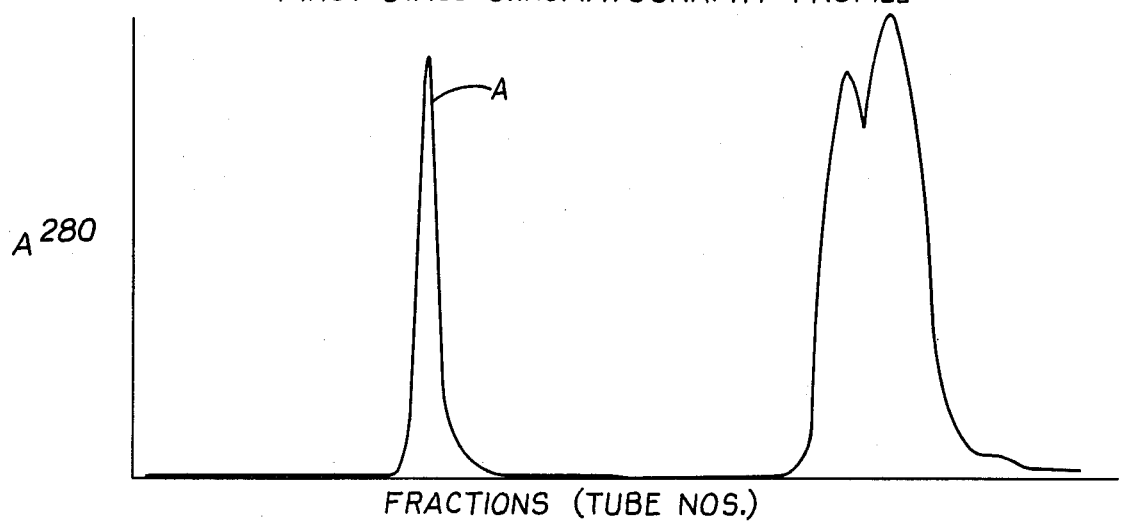
FIGS. 1-3 are respectively chromatography profiles developed as a result of first stage, second stage and third stage column chromatographies of ammonium sulfate fractionated Parvovirus-immunized positive goat serum in accordance with the preferred method of the invention.

The following examples set forth the most preferred method of producing biologic in accordance with the invention, along with a number of examples showing treatment of mammals with the biologic.

EXAMPLE I

This example sets forth the preferred procedures for the production and recovery of the biologic of the present invention.

Goat Vaccination

A total of five normal goats were initially hypervaccinated with Parvovirus in multiple sites on their dorsal rear halves, using a total of 1 cc. of commercially available Feline Pan Leukopenia vaccine (Dellen Laboratories, Inc., Westwood, Maine). Thereafter, at intervals of about one and two months after the initial injection, each goat was again injected with 1 cc. total quantities of Canine Origin Parvovirus vaccine (Fromm Laboratories, Inc., Grafton, Wis. or Duramune Vaccine, Temple, Tex.). At the end of about three months from the date of the initial injection, a sample of whole blood was withdrawn from the carotid artery of the neck of each goat, and the samples treated as hereinafter described.

Goat Plasma Preparation

The goat blood samples were separately centrifuged (about 500 ml. at a time) using a swinging bucket rotor centrifuge operated at 2000 rpm for 45 minutes to pellet the red blood cells. The plasma was then removed from the packed red cells in each sample, and volumetrically measured. An absorbance reading (280 nm) of each plasma sample diluted 1:50 with PBS (pH 7.5) was then taken for record purposes.

Serum Preparation

Reagents Employed:
1.0 molar Calcium Chloride
  14.7 gm $CaCl_2 2H_2O$ in 100 ml distilled water
Thrombin
  Miles Laboratories, Inc.
  Bovine Thrombin (500 units/ml)
  Reconstitute vial with:
    1.0 ml sterile saline
    1.0 ml glycerol
Saline
  0.9 gms Sodium Chloride in 100 ml distilled water
Procedure:
  Use 1.0 ml of 1. molar calcium chloride for each 100 ml of plasma.
  Use 100 ul of thrombin for each 100 ml of plasma.
1. The required amount of calcium chloride and thrombin was added to each measured plasma sample in a beaker.
2. The respective plasma/calciumchloride/thrombin mixtures were then stirred gently and thereafter each beaker was placed in a water bath at 37° C. for 30 minutes.
3. The beakers of clotted plasma were then removed from the water bath, and the plasma in each beaker cut up into small pieces.

4. Each mixture was then poured into a respective centrifuge tube, and the tubes were spun 10,000 rpm for 30 minutes.
5. Serum was then carefully removed from the clot at the bottom of each of the tubes to give separate serum samples.
6. The serum volume absorbance reading at 280 nm for each sample was then taken and recorded.

Biologic Determination

An in vitro assay was next performed on the serum samples derived from each of the test goats, in order to determine which of the goats produced the desired biologic in sufficient quantity. Normal human white cells were first cultured in RPMI-1640 media (a standard tissue culture media produced by K. C. Biological of Lenexa, Kans.) supplemented with 10% fetal calf serum. Fifty microliters of each of the goat test serums produced as described previously were then added to respective cultures each containing $2-4 \times 10^5$ cultured human white blood cells in a total volume of 2 ml. The cultures, with goat serum added, were then incubated in an atmosphere of 5% $CO_2$/95% air at 37° C. for 3 days. Each separate culture was then stained with two types of fluorescent-labeled monoclonal antibodies respectively specific against T-helper cells (OKT-4 monoclonal antibody sold by Ortho Diagnostic of Raritan, N.J.) and Natural Killer cells (LEU-7 monoclonal antibody sold by The Becton-Dickinson Co. of Mountain View, Calif.). The stainings were performed following the supplier's directions, and after about one hour, the stained samples were analyzed using a flow cytometry device, namely a model 50H cytofluorograph (Ortho Instruments, Westwood, Mass.) to count both T-helper and Natural Killer cells in each culture. The test animal serums were compared against a stained and counted control sample comprising cultured human white blood cells and 50 microliters of normal goat serum prepared as outlined previously. Those cultures which exhibited at least about a 50% increase in the number of T-helper cells and Natural Killer cells, as compared with the control, were considered positives for the biologic of the invention. In this specific test three of the five goat serum samples gave positive results; one sample gave about a 50% increase, whereas the other two samples gave an increase on the order of 125%.

The above described in vitro determination assay is used throughout the purification and isolation protocol in order to identify which of the separated fractions in each instance contained the desired biologic.

The three positive serum samples were each further treated as described below (the procedure for only a single serum sample is set forth, but the method of treating all the samples was the same). In this example, the respective positive serum samples were treated separately; however, such samples could be pooled if desired.

Ammonium Sulfate Fractionation

Reagents Employed:
Ammonium Sulfate (Sigma S-5182, Sigma Chemical Co., St. Louis, Mo.) 0.01 m Sodium Phosphate (pH 7.6)
Procedure:
1. 24.3 gm of ammonium sulfate was weighed out for each 100 ml of serum to be fractionated.
2. The serum sample was placed in a beaker and stirred. During stirring small amounts of ammonium sulfate were added, making sure that all was dissolved before adding more ammonium sulfate; this procedure was continued until entire amount of ammonium sulfate was added to the sample. The sample was then gently stirred for another 30 minutes.
3. The serum sample was then placed in a centrifuge tube and spun at 10,000 rpm for 30 minutes, whereupon supernatant was carefully removed from the pellet. The supernatant serum fraction was tested for the presence of the desired biologic using the in vitro cell culture assay described above under "Biologic Determination: and was found to be negative; this supernatant was therefore discarded.
4. The centrifuged pellet from step 3 was then redissolved in 0.01 m sodium phosphate (pH 7.6), with the final volume of redissolved pellet being the same amount as that of original serum volume.
5. Steps 2 and 3 were then repeated for the serum sample, in order to effect another separation; again, the in vitro determination assay confirmed that the supernatant did not contain the desired biologic.
6. The pellet was then redissolved to one-half of the original serum volume, using 0.01 m sodium phosphate (pH 7.6).
7. The resuspended material sample was then placed into a section of 12,000 mw cut-off dialysis tubing.
8. The sample was then dialyzed against 0.01 m sodium phosphate (pH 7.6), using three changes of 4 liters in the dialysis.
9. The sample was then removed from the dialysis tubing and put into a centrifuge tube.
10. The tube was next spun at 10,000 rpm for 30 minutes.
11. The supernatant from the centrifuge tube was then removed and the volume measured and recorded; another in vitro determination assay as described above was performed on the supernatant, to confirm that it did contain the desired biologic.
12. The absorbance at 280 nm for the supernatant was taken and recorded.
13. The supernatant material resulting from the fractionation of the sample was stored in a sterile bottle.

First Stage Chromatography (using DE-52 anion exchange resin, Whatman, Inc., Clifton, N.J.
1. An appropriate quantity of DE-52 resin was swelled and equilibrated in 0.01 molar Sodium Phosphate, pH 7.6.
2. A column (4.4 cm $\times$ 83 cm) was packed with swelled DE-52 resin. The colum was washed with 2 liters of 0.01 m $NaH_2PO_4$ (pH 7.6) at 75 cm pressure.
3. 40 ml of the ammonium sulfate fractionated serum from the sample were loaded onto the DE-52 column at the same pressure as the wash. The material was then eluted with 0.01 m $NaH_2PO_4$ (pH 7.6) wash.
4. Liquid from the column was collected in separate tubes (150 drops/tube—approximately 5.0 ml) until all protein fractions were completely eluted. About 1.0 liter of 0.01 molar $NaH_2PO_4$ was passed through the column.
5. The column was then washed with 1.5 liters of 0.01 molar $NaH_2PO_4$ containing 0.5 m NaCl (pH 7.6) to remove bound material from the column. Liquid from the columns was collected in separate tubes (150 drops/tube) until the buffer was expended.
6. The absorbance at 280 nm was taken for all tubes collected. A plot of absorbance ($A^{280}$) vs. tube number was prepared to locate the peaks. This graph is reproduced as FIG. 1.

7. The material within tubes located in each separate peak off the plot were then pooled and assayed using the described in vitro determination assay.
8. The pooled material from the first peak (peak A of FIG. 1) was found to contain the biologic of the invention. This material was concentrated by placing the material into a section of dialysis tubing and tying off the ends; the tubing was then placed into a tub of polyethylene glycol (20,000 mw, Sigma Chemical Co., St. Louis, Mo.) and concentrated to about 10% of the original pooled volume. The tubing was then rinsed well with water.
9. The pooled material within the tubing was then dialyzed against PBS (pH 7.5). Three changes of 4 liters were used to remove polyethylene glycol and salt.
10. The dialyzed material was then removed from tubing and the volume measured. Absorbance readings at 280 nm were taken and recorded along with volume.

Figure 2:
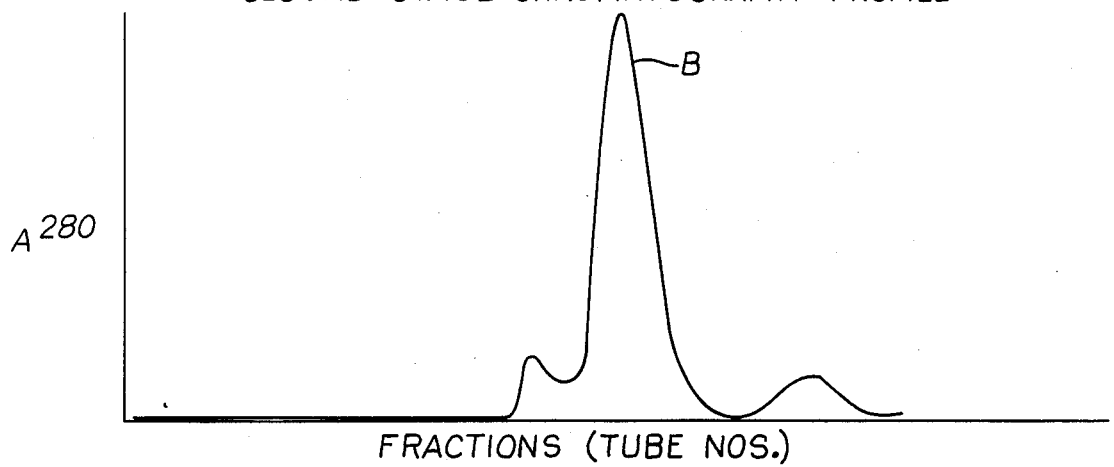

Second Stage Chromatography (using S-200 size exclusion chromatography resin, Sigma Chemical Co., St. Louis, Mo.)
1. An elution column (4.4 cm×83 cm) was packed and equilibrated with S-200 resin, and the column was washed with 2 liters of PBS (0.1 m $NaH_2PO_4$ containing 0.15 m NaCl, pH 7.5) at 60 cm. pressure.
2. 15 mls. of the pooled, dialyzed material from the first concentrated peak (peak A, FIG. 1) off of the DE-52 column was next loaded onto the S-200 column, and the sample was eluted using the PBS of step 1. The liquid off the column was collected in separate tubes (100 drops/tube, approximately 3.0 ml).
3. Absorbance readings at 280 nm were then taken for all of tubes collected. A plot of $A^{280}$ vs. tube number was then prepared; this plot is reproduced as FIG. 2.
4. The material within tubes located in each peak were pooled and concentrated with polyethylene glycol as set forth in steps 7 and 8 of the first stage chromatography procedure. The pooled samples were each then tested using the in vitro determination assay.
5. The pooled material from the largest peak (peak B, FIG. 2) was found to contain the biologic. This material was then dialyzed using dialysis tubing against 3 changes of 4 liters of PBS (0.01 m $K_2HPO_4$ containing 0.15 m NaCl, pH 7.5).
6. The dialyzed material was then removed from the tubing and the volume measured and recorded. An absorbance ($A^{280}$) was then taken on the dialyzed material, and the reading recorded.

Figure 3:
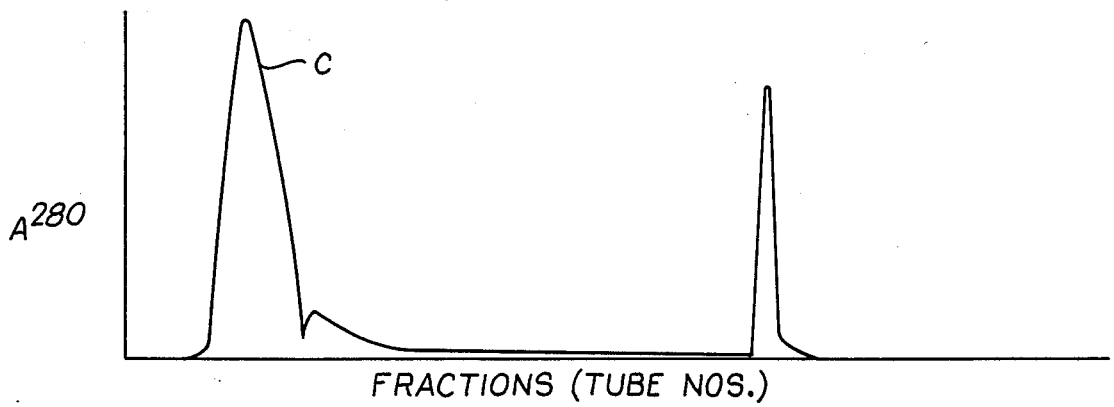

Third Stage Gel Chromatography (using CM Blue AFFI gel cation exchange resin, Bio-Rad Corp., Richmond, Calif.)
1. A column (1.5 cm×38 cm) was packed and equilibrated with the CM Blue AFFI gel, and the column was washed with 2 liters of 0.01 m $K_2HPO_4$ containing 0.15 m NaCl, pH 7.25, at 45 cm pressure. The column was next washed with 500 ml of $K_2HPO_4$ buffer.
2. 8 ml of material concentrated from the largest peak off the S-200 column (peak B, FIG. 2) was then loaded onto the column.
3. The column was then washed with 0.01 m $K_2HPO_4$ containing 0.15 m NaCl (pH 7.25) until all peaks were eluted, using approximately 150-200 ml PBS for the column. Liquid off the column was collected in separate tubes (90 drops/tube, about 2 ml).
4. The column was again washed with 200 ml of 0.01 m $K_2HPO_4$ containing 0.5 m NaCl (pH 7.25) to further elute the bound material; liquid off column was collected in tubes (90 drops/tube).
5. Absorbance readings at 280 nm were taken for all tubes and a plot of $A^{280}$ vs tube number from both elutions was prepared; this plot is reproduced as FIG. 3. Material within each peak was pooled, and these were assayed using the in vitro determination assay.
6. Material from the first peak (peak C, FIG. 3) was found to contain the biologic; this material was concentrated with polyethylene glycol as described above in the first stage chromatography procedure.
7. The concentrated material was next dialyzed against PBS, using three changes of 4 liters each.
8. The material was next removed from dailysis tubing. Absorbance at 280 nm was read and recorded.
9. The material was filtered using 0.2 μm filter and stored.

As is evident from the foregoing, after a determination is made for the positive serum samples (i.e., those containing adequate amounts of biologic) successive fractionation and separation techniques may be employed to obtain the relatively purified biologic material, with appropriate assays being performed on separated fractions in order to ensure that the biologic is retained throughout. The final biologic product comprises proteinaceous component(s) which have not to date been completely characterized. However, the product is presently believed to be an interleukin protein or proteins having an apparent molecular weight in the range of 100,000 to 120,000 daltons; the components also appear to be glycosylated. A sample of the purified biologic made in accordance with the present invention has been deposited with the American Type Culture Collection; such sample has been accorded accession number 40105. Obviously, however, there is no desire to be bound to any preliminary or partial characterizations, and such are offered only in an effort to disclose all presently available pertinent information.

While the above described separation and isolation procedures are in many cases preferred, it should be understood that the biologic product derived from the methods of the invention can be used without such purifications, particularly if used in connection with animals. In the latter case, the fractionated positive goat serum can be used, inasmuch as such a relatively crude material contains the desired proteinaceous component(s), while potentially interfering interleukins have been removed.

EXAMPLE II

Treatment of a Human with Biologic for Lowering Serum Cholesterol Levels

A female patient was treated with a purified biologic produced in accordance with Example I on five occasions. The injections were I.V. in 10 cc of saline. The first three treatments were on three consecutive days. A total of 150 micrograms of the biologic was given in three (3) evenly divided doses. Two weeks later the patient was treated with 2 mg of the purified biologic in two (2) evenly divided doses on two (2) consecutive days. The patient's serum was obtained on multiple occasions and analyzed for cholesterol and triglyceride content. No adverse side effects were noted in the patient. The data are presented in Table 1:

TABLE 1

THE EFFECT OF BIOLOGIC ISOLATED FROM GOAT ON SERUM CHOLESTEROL AND TRIGLYCERIDES CONCENTRATION IN A HUMAN[1]

| Date | Amount Injected | Serum Sample Taken (X) | Serum Concentration[2] Cholesterol | Triglycerides |
|---|---|---|---|---|
| July 18 | — | X | 220 mg/0.1 liter | 82 mg/0.1 liter |
| Dec. 19 | 50 ug | X | 201 | 90 |
| Dec. 20 | 50 ug | — | — | — |
| Dec. 21 | 50 ug | X | 178 | 88 |
| Jan. 4 | 1 mg | X | 157 | 110 |
| Jan. 5 | 1 mg | — | — | — |
| Jan. 6 | — | X | 161 | 89 |
| Jan. 15 | — | X | 145 | ND |

[1] Prior to treatment the patient was tested for allergy to goat protein by intradermal injection of 200 ul of the biologic. No reaction was present after 2 days.
[2] Serum from the patient's blood was analyzed using a Technicom Instruments SMAC analyzer to determine cholesterol and triglyceride concentration.

This test demonstrated a substantial decrease in serum cholesterol levels, although there was no decrease in triglyceride concentration with this patient.

EXAMPLE III

Treatment of a Rabbit with the Biologic to Reduce Serum Cholesterol Concentration A female rabbit was treated for one week with the biologic. In this instance, however, the material tested had been purified only through the ammonium sulfate fractionation and the first stage chromatography steps described in Example I; thus the biologic was in a relatively crude, unpurified form. The rabbit was injected daily with 0.25 ml of the crude biologic for five consecutive days. The biologic was administered by I.V. in the ear vein. Blood for analysis was collected from an ear vein of the rabbit and allowed to clot. The serum was analyzed on a Technicon Instruments SMAC analyzer. A sample was drawn the day the experiment began to establish a baseline. The data are presented in Table 2. Food and water were provided ad lib during the experiment.

TABLE 2

EFFECT OF CRUDE BIOLOGIC ON SERUM CHOLESTEROL AND TRIGLYCERIDE CONCENTRATIONS IN A RABBIT[1]

| Date | Cholesterol | Triglycerides |
|---|---|---|
| September 28 | 151 mg/0.1 liter | 82 mg/0.1 liter |
| October 6 | 82 | 43 |
| October 31 | 37.8 | 24 |

[1] The rabbit was treated daily with 0.25 ml of the crude biologic for five days by I.V. Injection. The biologic had a protein concentration of 12 mg/ml, as measured by absorbance at 280 nm.

This example demonstrates a reduction in both cholesterol and triglyceride concentration in the rabbit, using the crude biologic of the invention.

EXAMPLE IV

Treatment of a Dog Infected with *E. canis* using Biologic

*Ehrlichia canis* is a rickettsia-like organism that is transmitted by ticks. Currently it is believed to be infectious only in dogs and horses, and in the case of dogs is usually fatal. The tissue parasitized by *E. canis* is peripheral leukocytes, and the organism causes inactivation or destruction of white blood cell producing stem cells. A dog was diagnosed on November 10 with *Ehrlichia canis*, and exhibited a 0–400 white blood count (WBC), a 10–20 hematocrit, and gram positive bodies present in peripheral white cells. The dog's initial therapy consisted of weekly transfusions with whole blood with the last transfusion given on December 6. Prior to treatment with the biologic, histological examination of the dog's bone marrow demonstrated that the marrow was aplastic with no active regions. On December 12 the dog was first treated with the biologic of the invention, which in this case was a relatively crude ammonium sulfate fractionated proteinaceous mixture described in Example I (no chromatography separations performed on this material). The dog was injected with 21 mg. of the crude fractionated material suspended in 1 cc. of saline. After 4 days the dog's WBC rose from 800 to 6300 cells/mm$^3$. The animal was thereafter treated on two more occasions, using the same dosage. Fifteen days after the last treatment, the dog had a white cell count of 2,800 cells/mm$^3$ and a hematocrit of 25. After about 4 months (without further treatments) the dog exhibited no syptoms of *E. canis* infection. The data is presented below:

TABLE 3

EFFECT OF BIOLOGIC ON *E. CANIS* INFECTED DOG

| Treatment | Day | WBC | PVC |
|---|---|---|---|
| 21 mg | 12-12 | 800 cells/mm$^3$ | 22 |
|  | 12-16 | 6,300 | 23 |
|  | 12-20 | 2,900 | 23 |
| 21 mg. | 12-23 | 5,400 | 24 |
| 21 mg. | 12-26 | 8,800 | 24 |
|  | 1-3 | 3,900 | 23 |
|  | 1-10 | 2,800 | 25 |

This test demonstrated that the biologic of the invention acts as an immunomodulator by stimulating viable stem cells in the dog; this result is confirmed by the large increase in WBC experienced subsequent to treatment, and the apparent cure effected.

EXAMPLE V

Blast Transformation Assay with Biologic Isolated from Goat

Normal human lymphocytes were first isolated using conventional techniques by centrifugation in a density media of Ficoll-Histopaque. The separated white cells were next suspended in tissue culture media (RPMI-1640) containing 10% fetal calf serum and then pipetted into tissue culture flasks (2 mls/flask). Twenty-five microliters of the crude, ammonium sulfate fractionated, goat-derived biologic produced as described in Example I was then added to each test flask. The cultures were then incubated for 3 days and washed with saline. The cells in each culture were then resuspended in phosphate buffered saline and stained with fluorescent labeled mouse antihelper (OKT-4) or mouse anti-suppressor (OKT-8) monoclonal antibody; Ortho Diagnostic, Raritan, N.J. The stained cells were then analyzed on the 50H Cytofluorograph. Control flasks were also provided which isolated cells suspended in equal amounts of the RPMI-1600 FCS media, plus an amount of non-immunized normal goat sera equal in volume to the volume of biologic added to the test cultures. The data from this experiment are presented in Table 4:

TABLE 4

IN VITRO BLAST TRANSFORMATION ASSAY FOR HUMAN LYMPHOCYTES STIMULATED WITH BIOLOGIC ISOLATED FROM VIRALLY VACCINATED GOATS

| Culture | Lymphocytes (Number) Helper | Suppressors | Ratio Helper/Suppressor |
|---|---|---|---|
| Control with Normal Goat Serum | 3166 | 4441 | 0.788 |
| With Biologic | 4335 | 4408 | 1.36 |

This in vitro assay demonstrates that the biologic of the invention acts as an immunostimulant in cell culture. The rise in Helper/Suppressor ratio is particularly significant.

EXAMPLE VI

Effect of Biologic on Treatment of Footrot in Sheep

A herd of 109 sheep infected with footrot was treated with the crude, ammonium sulfate-fractionated goat-derived biologic produced in accordance with the method of Example I. Fifty-nine of the sheep presented clinical symptoms of footrot, with the animals in the most advanced stages of the disease being unable to walk. These animals were missing a substantial portion of their footpads due to the disease, and were forced to crawl on their knees.

All of the 109 sheep in the herd were given a single intramuscular injection of the goat-derived biologic, and the sheep were then observed daily thereafter for 10 days. Each sheep was given a dose of 1 cc. of the crude biologic.

Following treatment, no new cases of footrot occurred. Within 10 days the animals previously unable to walk were up and walking again. On observation, the footpads of these animals were no longer red and wet, and a new footpad was growing and appeared to be whitish in color. The flock has subsequently been observed for an additional 30 days, with no recurrence of symptomatic footrot, and it is believed on the basis of this evidence that a cure was effected.

I claim:

1. A method of producing a glycosylated immunomodulating and serum cholesterol and triglyceride level decreasing protein biologic having an apparent molecular weight of above about 100,000, comprising the steps of:

injecting a feline panleukopenia or canine origin parvovirus into an animal other than a feline or canine, and which is a non-permissive host for the virus;

permitting said injected animal to react to the presence of said virus for a period of time of at least one month for developing in the animal's blood serum said biologic such that 50 microliters of the animal's serum, when added to an in vitro human white blood cell culture containing $2-4 \times 10^5$ white blood cells and followed by three days incubation at 37° C. under a 5% $CO_2$/95% air atmosphere, will give rise to at least about a 50% increase in T-Helper and Natural Killer cells in the biologic-supplemented cell culture as compared with an otherwise identical and identically cultured in vitro cell culture having added thereto 50 microliters of serum from a normal animal of the same species as said injected animal, such rise in T-Helper and Natural Killer cells being detected by staining with fluorescent-labelled monoclonal antibodies against T-Helper and Natural Killer cells; and recovering blood from said injected animal containing said biologic, and fractionating the recovered blood to separate potentially interfering substances from the biologic.

2. The method of claim 1, said animal being selected from the group consisting of goats, horses, sheep, rabbits and monkeys.

3. The method of claim 2, said animal being a goat.

4. The method of claim 1, including the step of repeatedly injecting said animal with said virus at spaced intervals after the initial injection.

* * * * *